United States Patent [19]

Paul et al.

[11] Patent Number: 4,742,169

[45] Date of Patent: * May 3, 1988

[54] PROCESS FOR THE PREPARATION OF HALOHYDROXYALKYL CARBAMATES AND 2,3-EPOXY CARBAMATES

[75] Inventors: Marsha A. Paul, Natick; George A. Doorakian, Bedford, both of Mass.

[73] Assignee: The Dow Chemical Company, Midland, Mich.

[*] Notice: The portion of the term of this patent subsequent to Feb. 26, 2002 has been disclaimed.

[21] Appl. No.: 720,447

[22] Filed: Apr. 5, 1985

[51] Int. Cl.$^4$ ............................................. C07D 241/04
[52] U.S. Cl. ..................... 544/388; 544/357; 544/385; 544/386; 544/54; 544/58.4; 544/88; 544/172; 546/226; 546/245; 548/201; 548/215; 548/341; 549/539; 560/115; 560/158; 560/166
[58] Field of Search ............... 544/385, 357, 388, 386, 544/54, 58.4, 88, 172; 546/226, 245; 548/201, 215, 341; 549/539; 560/115, 158, 166

[56] References Cited

U.S. PATENT DOCUMENTS 3,872,097 3/1975 Habermeier et al. ............... 544/374
4,501,874 2/1985 Hanafin ............................ 544/374

*Primary Examiner*—Glennon H. Hollrah
*Assistant Examiner*—James H. Turnipseed

[57] ABSTRACT

The invention is a process for the preparation of halohydroxyalkyl carbamates which comprises contacting an epihalohydrin carbonate with a secondary amine-containing compound, wherein the secondary amine has a pKa at which the secondary amine will react with the epihalohydrin carbonate and which does not catalyze the formation of unwanted by-products in the further presence of an acid scavenger capable of forming a salt with the hydrogen halide by-product formed, in an amount sufficient to prevent the formation of unwanted by-products, in a polar organic solvent under conditions such that a halohydroxyalkyl carbamate, wherein the carbamate nitrogen is tertiary, is prepared.

Another aspect of this invention is the further step of contacting the 3-halo-2-hydroxyalkyl carbamate with an ion-exchange resin with pendant moieties containing hydroxide moieties in a lower alkanol solvent under conditions such that the 3-halo-2-hydroxyalkyl moieties are converted to 2,3-epoxyalkyl moieties so as to prepare a 2,3-epoxyalkyl carbamate.

29 Claims, No Drawings

PROCESS FOR THE PREPARATION OF HALOHYDROXYALKYL CARBAMATES AND 2,3-EPOXY CARBAMATES

BACKGROUND OF THE INVENTION

This invention relates to the preparation of halohydroxyalkyl carbamates and the conversion of such products to 2,3-epoxy carbamates.

The 2,3-epoxy carbamates are useful as reactive diluents, in ultraviolet light stable epoxy resins, as additives to reduce the brittleness of epoxy resins, and as crosslinking agents in epoxy resins, polyurethanes and epoxy novolak systems.

Doss, U.S. Pat. No. 3,440,230, discloses a process for the preparation of a carbamate in which a polyisocyanate is reacted with an epoxy alcohol so as to form a carbamate in which the carbamate nitrogen has an active hydrogen atom attached thereto. The reaction to form the carbamate may be represented by the following equation:

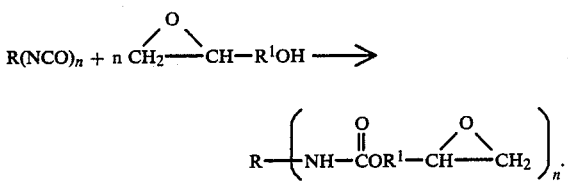

See also Kaufmann, U.S. Pat. No. 3,484,413 and Tesoro, U.S. Pat. No. 3,684,429. As described hereinbefore, the compounds made by this process result in a carbamate in which the carbamate nitrogen has an active hydrogen atom attached. Such compounds easily rearrange to prepare cyclic compounds, in particular, 4-hydroxymethyl-1,3-oxazolidin-2-ones. See U.S. Pat. No. 3,484,413 and Farrissey et al., *J. of Heterocyclic Chem.*, 7, 331 (1970). This formation of cyclic compounds is undesirable as such rearrangements result under conditions at which the epoxy carbamates would normally be used.

SUMMARY OF THE INVENTION

The invention is a process for the preparation of halohydroxyalkyl carbamates which comprises contacting an epihalohydrin carbonate with a secondary amine-containing compound, wherein the secondary amine has a pKa at which the secondary amine will react with the epihalohydrin carbonate and which does not catalyze the formation of unwanted by-products in the further presence of an acid scavenger capable of forming a salt with any hydrogen halide by-product formed, in an amount sufficient to prevent the formation of unwanted by-products, in a polar organic solvent under conditions such that a halohydroxyalkyl carbamate, wherein the carbamate nitrogen is tertiary, is prepared.

Another aspect of this invention is the further step of contacting the 3-halo-2-hydroxyalkyl carbamate with an ion-exchange resin with pendant moieties containing hydroxide moieties in a lower alkanol solvent under conditions such that the 3-halo-2-hydroxyalkyl moieties are converted to 2,3-epoxyalkyl moieties so as to prepare a 2,3-epoxyalkyl carbamate.

DETAILED DESCRIPTION OF THE INVENTION

The products of this process are halohydroxyalkyl carbamates, both 1-halo-2-hydroxyalkyl carbamates and 3-halo-2-hydroxyalkyl carbamates can be prepared by this process. The preferred halohydroxyalkyl carbamates are the 3-halo-2-hydroxyalkyl carbamates as they can be converted to 2,3-epoxyalkyl carbamates. The choice of solvent has a significant effect on the ratio of the two products.

Included among the 3-halo-2-hydroxyalkyl carbamates with tertiary carbamate nitrogen atoms prepared by this invention are the 3-halo-2-hydroxyalkyl carbamates and poly-(3-halo-2-hydroxyalkyl) polycarbamates. Preferred 3-halo-2-hydroxyalkyl carbamates are 3-halo-2-hydroxyalkyl dialiphatic or dialicyclic carbamates and 3-halo-2-hydroxyalkyl cycloalkylene carbamates. Preferred poly-(3-halo-2-hydroxyalkyl) polycarbamates are poly-(3-halo-2-hydroxyalkyl) N-aliphatic or N-alicyclic alkylene polycarbamates, or bis-(3-halo-2-hydroxyalkyl) 1,4-piperazinyl dicarboxylates. In one more preferred embodiment, the 3-halo-2-hydroxyalkyl carbamates with tertiary nitrogen atoms are the poly-(3-halo-2-hydroxyalkyl) N-aliphatic or N-alicyclic alkylene polycarbamates or the bis-(3-halo-2-hydroxyalkyl) 1,4-piperazinyl dicarboxylates.

Of the 3-halo-2-hydroxyalkyl carbamates, the 3-halo-2-hydroxypropyl carbamates are more preferred, examples of which include 3-halo-2-hydroxypropyl dialiphatic or dialicyclic carbamates, 3-halo-2-hydroxypropyl cycloalkylene carbamates, poly-(3-halo-2-hydroxypropyl) N-aliphatic or N-alicyclic alkylene polycarbamates or bis-(3-halo-2-hydroxypropyl) 1,4-piperazinyl dicarboxylates; of which poly-(3-halo-2-hydroxypropyl) N-aliphatic or N-alicyclic alkylene polycarbamates and bis-(3-halo-2-hydroxypropyl) 1,4-piperazinyl dicarboxylates are even more preferred.

Among preferred 3-halo-2-hydroxyalkyl carbamates in this invention are those which correspond to the formulas

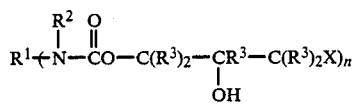

or

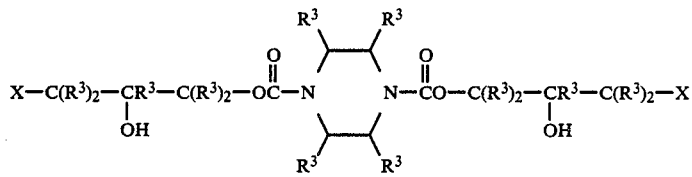

wherein
- R¹ is separately in each occurrence an n valent aliphatic or cycloaliphatic hydrocarbon;
- R² is separately in each occurrence an aliphatic or cycloaliphatic moiety;
- R³ is separately in each occurrence hydrogen or an aliphatic moiety;
- X is Br, Cl or I; and
- n is an integer of 1 to 6;

wherein R¹ and R² may be joined to form a cycloaliphatic moiety which can contain the heteroatoms O, N or S.

Preferred 3-halo-2-hydroxyalkyl carbamates include the following: (1) a 3-halo-2-hydroxyalkyl dialiphatic or dialicyclic carbamate which corresponds to the formula

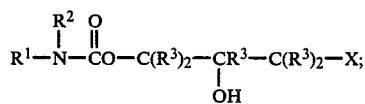

(2) a poly-(3-halo-2-hydroxyalkyl) N-aliphatic or N-alicyclic alkylene polycarbamate which corresponds to the formula

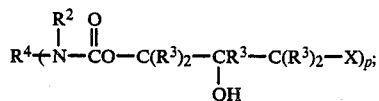

(3) a 3-halo-2-hydroxyalkyl cycloalkylene carbamate which corresponds to the formula

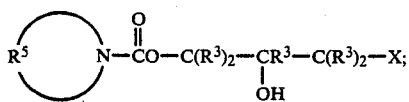

or (4) a bis-(3-halo-2-hydroxyalkyl) 1,4-piperazinyl dicarboxylate which corresponds to the formula wherein
- R¹ is separately in each occurrence an aliphatic or cycloaliphatic hydrocarbon;
- R² is separately in each occurrence an aliphatic or cycloaliphatic moiety;
- R³ is separately in each occurrence hydrogen or an aliphatic moiety;
- R⁴ is a p valent aliphatic or cycloaliphatic hydrocarbon;
- R⁵ is an alkylene radical, which can contain a heteroatom of O, S or N, which together with the carbamate nitrogen atom forms an aliphatic heterocyclic ring;
- X is Br, Cl or I; and
- p is an integer of between 2 and 6, inclusive.

The 3-halo-2-hydroxyalkyl carbamates can be converted to 2,3-epoxyalkyl carbamates. Included among the 2,3-epoxyalkyl carbamates with tertiary carbamate nitrogen atoms are the 2,3-epoxyalkyl carbamates and poly-(2,3-epoxyalkyl) polycarbamates. Preferred 2,3-epoxyalkyl carbamates are 2,3-epoxyalkyl dialiphatic or dialicyclic carbamates and 2,3-epoxyalkyl cycloalkylene carbamates. Preferred poly-(2,3-epoxyalkyl) polycarbamates are poly-(2,3-epoxyalkyl) N-aliphatic or N-alicyclic alkylene polycarbamates, or bis-(2,3-epoxyalkyl) 1,4-piperazinyl dicarboxylates. In one more preferred embodiment, the 2,3-epoxyalkyl carbamates with tertiary nitrogen atoms are the poly-(2,3-epoxyalkyl) N-aliphatic or N-alicyclic alkylene polycarbamates or the bis-(2,3-epoxyalkyl) 1,4-piperazinyl dicarboxylates.

Of the 2,3-epoxyalkyl carbamates, the epoxypropyl carbamates are more preferred, examples of which include 2,3-epoxypropyl dialiphatic or dialicyclic carbamates, 2,3-epoxypropyl cycloalkylene carbamates, poly-(2,3-epoxypropyl) N-aliphatic or N-alicyclic alkylene polycarbamates or bis-(2,3-epoxypropyl) 1,4-piperazinyl dicarboxylates; of which poly-(2,3-epoxypropyl) N-aliphatic or N-alicyclic alkylene polycarbamates and bis-(2,3-epoxypropyl) 1,4-piperazinyl dicarboxylates are even more preferred.

Among preferred 2,3-epoxyalkyl carbamates in this invention are those which correspond to the formulas

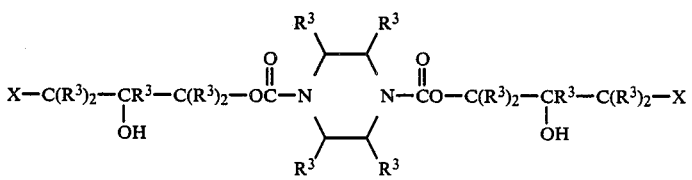

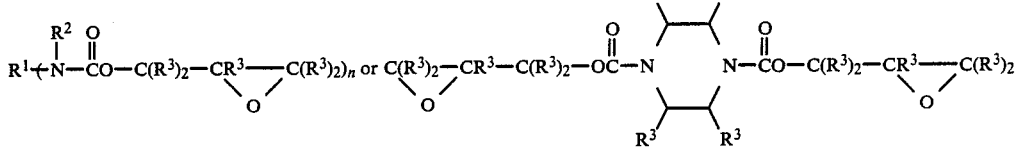

wherein $R^1$, $R^2$, $R^3$ and $R^4$ are as hereinbefore defined.

Preferred 2,3-epoxyalkyl carbamates include the following: (1) a 2,3-epoxyalkyl dialiphatic or dialicyclic carbamate which corresponds to the formula

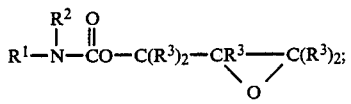

(2) a poly-(2,3-epoxyalkyl) N-aliphatic or N-alicyclic alkylene polycarbamate which corresponds to the formula

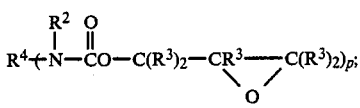

(3) a 2,3-epoxyalkyl cycloalkylene carbamate which corresponds to the formula

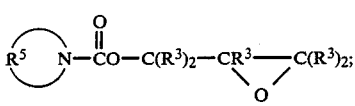

or (4) a bis-(2,3-epoxyalkyl) 1,4-piperazinyl dicarboxylate which corresponds to the formula

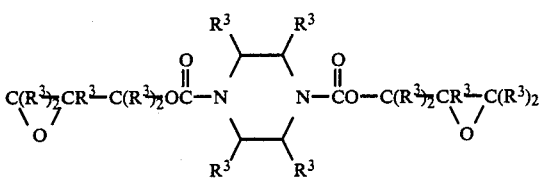

wherein $R^1$, $R^2$, $R^3$, $R^4$, $R^5$ and p are as hereinbefore defined.

In the hereinbefore-described formulas, $R^1$ is preferably a $C_{1-20}$ aliphatic or $C_{3-20}$ cycloaliphatic radical; more preferably a $C_{1-20}$ alkyl radical; and most preferably a $C_{1-10}$ alkyl radical. $R^2$ is preferably a $C_{1-20}$ aliphatic radical or a $C_{3-20}$ cycloaliphatic radical; more preferably a $C_{1-20}$ alkyl radical; and most preferably a $C_{1-10}$ alkyl radical. $R^3$ is preferably hydrogen or a $C_{1-20}$ aliphatic radical; more preferably hydrogen or a $C_{1-20}$ alkyl radical; even more preferably hydrogen or a $C_{1-3}$ alkyl radical; and most preferably hydrogen. $R^4$ is preferably a p-valent $C_{1-20}$ aliphatic or $C_{3-20}$ cycloaliphatic hydrocarbon radical; more preferably a p-valent $C_{1-20}$ alkyl radical; and most preferably a p-valent $C_{1-10}$ akyl radical. The

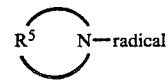

preferably forms a piperidine, pyrrolidine, oxazine, imidazolidine, morpholine, ethyleneamine, 3-pyrroline, or perhydro-1,3-thiazine ring; more preferably a piperidine, pyrrolidine, oxazine, or morpholine ring; and most preferably a pyrrolidine or piperidine ring. Preferably, n is between about 2 and 4, inclusive, and is most preferably 2. Preferably, p is between 2 and 4, inclusive, and is most preferably 2.

For use in this invention any epihalohydrin carbonate which will react with a secondary amine with a suitable pKa can be used in this process. Included among desirable epihalohydrin carbonates (4-(1-haloalkyl)dioxolan-2-ones) are those which correspond to the formula

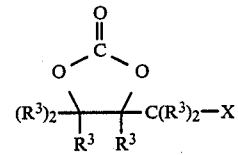

wherein $R^3$ is as defined hereinbefore and X is iodine, chlorine, or bromine. X is preferably bromine or chlorine and most preferably chlorine. Examples of epihalohydrin carbonates include epiiodohydrin carbonate, epichlorohydrin carbonate and epibromohydrin carbonate. In preferred embodiments, the epihalohydrin carbonate is 99 percent pure. When epihalohydrin carbonates of such purity are used, the products prepared are of higher purity and are more stable.

The amines useful in this invention include all secondary amines which have a pKa at which the amines react with an epihalohydrin carbonate and do not catalyze the formation of unwanted by-products. Secondary amines with pKa's which are too low will not react with epichlorohydrin carbonates. Secondary amines with pKa's which are too high result in the formation of polymeric by-products. Preferred secondary amines are those with pKa's of between about 6 and 12. Desirable secondary amines include those which correspond in the formula

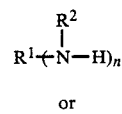

or

-continued

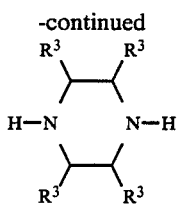

wherein $R^1$, $R^2$, $R^3$ and N are as hereinbefore defined.
Preferred secondary amines include aliphatic secondary amines which correspond to the formula

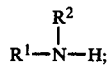

heterocyclic secondary amines which correspond to the formula aliphatic secondary polyamines which correspond to the formula

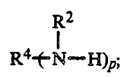

or piperazines which correspond to the formula

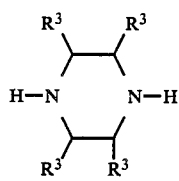

wherein
$R^1$ is separately in each occurrence an aliphatic or cycloaliphatic radical;
$R^2$ is separately in each occurrence an aliphatic or cycloaliphatic radical;
$R^3$ is separately in each occurrence hydrogen or an aliphatic radical;
$R^4$ is a p valent aliphatic or cycloaliphatic hydrocarbon;
$R^5$ is an alkylene radical which can contain a heteroatom of O, S or N, which together with the nitrogen forms an aliphatic heterocyclic ring; and
p is an integer between 2 and 6, inclusive.

It is more preferable that the secondary amines useful in this invention have a pKa of between 7.5 and 12. Among more preferred amines are the aliphatic secondary polyamines and piperazine.

Examples of secondary amines useful in this invention are dimethylamine, diethylamine, di-n-propylamine, diisopropylamine, di-n-butylamine, di-sec-butylamine, dipentylamines, dihexylamines, dioctylamines, ditriacontenylamine, N-methyl ethylamine, N-methyl propylamine, N-methyl octadecylamine, N-ethyl hexylamine, N-ethyl dodecylamine, N-propyl dodecylamine and the like.

Examples of heterocyclic aliphatic secondary amines include piperidine, pyrrole, imidazolidine, pyrazole, piperazine and the like.

The process for the preparation of the 3-halo-2-hydroxyalkyl carbamates is exemplified by the following equations:

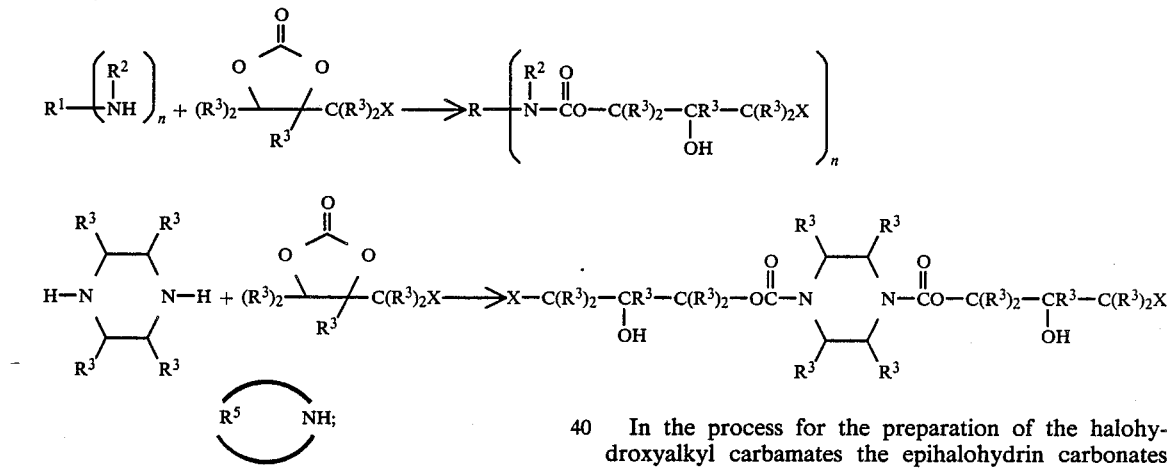

In the process for the preparation of the halohydroxyalkyl carbamates the epihalohydrin carbonates are contacted with the secondary amines in an equivalent ratio of between about 0.01:1.0 and 100:1.0, preferably in an equivalent ratio of between about 20:1.0 and 1.0:1.0, and most preferably in an equivalent ratio of between about 2.0:1.0 and 1.0:1.0. An equivalent of amine means herein that amount of a secondary amine which will react with one mole of an epihalohydrin carbonate to give the desired halohydroxyalkyl carbamates.

The secondary amine and epihalohydrin carbonate are contacted in a polar organic solvent. Examples of desirable polar organic solvents include acetonitrile, tetrahydrofuran, dioxane, and lower alkanols. Wherein the halohydroxyalkyl carbamates are to be converted to the epoxyalkyl carbamates, the preferred solvents are the lower alkanols, with ethanol being the most preferred. If 2,3-epoxyalkyl carbamates are to be prepared from the 3-halo-2-hydroxyalkyl carbamates, the lower alkanols are the preferred solvents. The polar aprotic solvents are preferred when the amount of 1-halo-2-hydroxyalkyl carbamates is to be minimized, as the use of such solvents results in little or no 1-halo-2-hydroxyalkyl carbamates.

In general, the ratio of solvents to reactants is any ratio in which the reactants are dissolved. It is preferred that the weight ratio of solvent to epihalohydrin carbonate be 5.0:1.0 or greater.

The preparation of the halohydroxyalkyl carbamates can proceed at any temperature at which the epihalohydrin carbonate reacts with the secondary amine. Preferable temperatures are between about 0° C. and 100° C., with between 0° C. and 40° C. being preferred. If the reaction is run below 0° C., excessively long reaction times are required, while at temperatures of greater than 100° C., side reactions, including the formation of the epoxide group followed by reaction with unreacted amine can lead to the formation of oligomers and by-products.

This process is usually carried out for a period of time sufficient for the amine to react completely with epihalohydrin carbonate and can vary from between about 5 minutes and 48 hours, dependent upon the amine, temperature, and solvent chosen. Preferred reaction times are between about 1 and 24 hours.

This process may be run at any pressure at which the reaction proceeds. Atmospheric pressure is preferred. It is preferable to run this reaction in an inert gas atmosphere, for example, under a nitrogen or argon atmosphere.

It is preferable to add an acid scavenger during this step. Compounds which form salts with hydrogen halide and are inert to the reactants are suitable. Examples of preferable acid scavengers are alkali metal bicarbonates and alkaline earth metal bicarbonates. More preferred acid scavengers are sodium and potassium bicarbonates. The acid scavengers react with any hydrogen halide formed during the process to prevent the formation of unwanted by-products due to the presence of the hydrogen halide. As a result, the product can be recovered in higher purity. A sufficient amount of acid scavenger to prevent the formation of by-products is suitable. Preferably the equivalent ratio of acid scavenger to amine is between about 0.05:1 and 5:1, more preferably between 1:1 and 3:1, and most preferably between about 1.01:1 to 1.10:1.

The halohydroxyalkyl carbamates can be recovered and isolated by removing the solvent of the reaction mixture. The solvent can be removed by evaporation. Thereafter, the remainder which generally comprises the halohydroxyalkyl carbamates and epihalohydrin carbonate is dissolved in a slightly polar solvent and passed through a silica adsorbent. A preferable solvent is a 50/50 mixture of chloroform (trichloromethane) and methylene chloride (dichloromethane). The halohydroxyalkyl carbamate is adsorbed while the epihalohydrin carbonate passes through the adsorbent. The halohydroxyalkyl carbamate can be desorbed from the silica by passing a desorbent through the adsorbent. Suitable desorbents are liquids which are strongly polar and dissolve the halohydroxyalkyl carbamates. Preferred desorbents are the alkanols, with methanol or ethanol being most preferred. The desorbent can thereafter be evaporated away to leave the product.

Alternatively, the halohydroxyalkyl carbamate can be recovered by removing the reaction solvent by evaporation, dissolving the concentrated reaction mixture in a chlorinated aliphatic hydrocarbon and washing the solution with a mildly acidic aqueous solution. Preferably, the aqueous solution contains less than 10 percent by weight of a protic acid, more preferably less than 5 percent by weight. A preferred protic acid is hydrochloric acid. A preferred solvent is methylene chloride.

The 3-halo-2-hydroxyalkyl carbamates so recovered can thereafter be used to prepare a 2,3-epoxyalkyl carbamate. It is not necessary to isolate the 3-halo-2-hydroxyalkyl carbamate to prepare a 2,3-epoxyalkyl carbamate provided the reaction solvent used to prepare 3-halo-2-hydroxyalkyl carbamate is a lower alkanol.

The 3-halo-2-hydroxyalkyl carbamates are converted to 2,3-epoxyalkyl carbamates by contacting the 3-halo-2-hydroxyalkyl carbamates with a polymeric backbone with pendant moieties which contain hydroxide moieties. This process step is exemplified by the following equations:

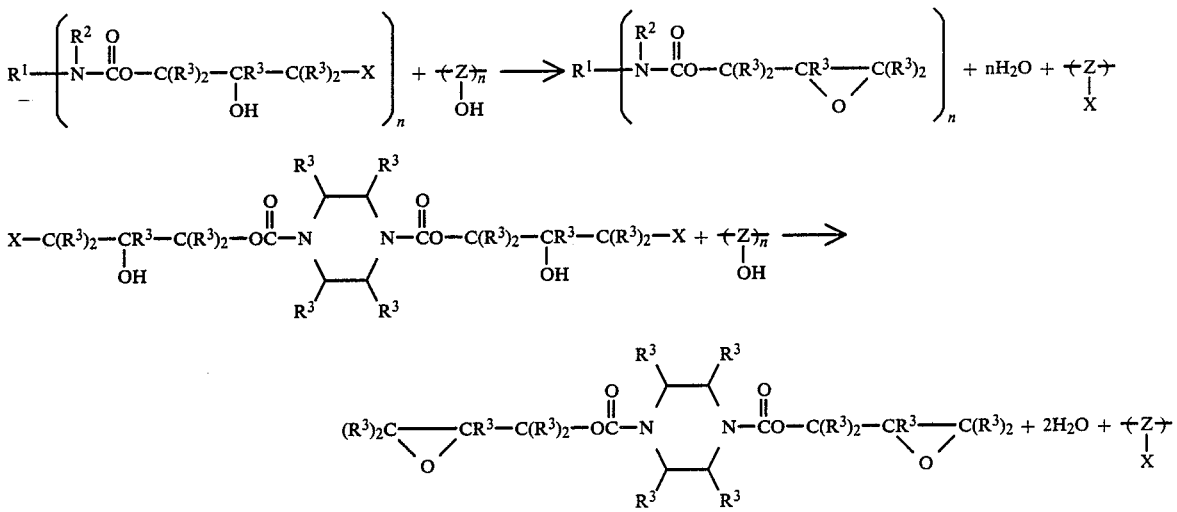

wherein $R^1$, $R^2$, $R^3$, X and n are as defined hereinbefore; and Z is the repeating unit of a polymeric backbone resin.

The hydroxide moiety is supported in a manner such that it is a pendant moiety from a polymeric backbone. An example of this is an ion-exchange resin wherein the hydroxide moiety is pendant.

Especially preferred as polymers employed in providing pendant hydroxide moieties which are useful in the practice of the present invention are cross-linked polymers formed by the addition copolymerization of polymerizable monoethylenically unsaturated monomer or a mixture of such monomer with a cross-linking agent copolymerizable therewith, typically a polyethylenically unsaturated monomer such as divinylbenzene. Suitable polymerizable monoethylenically unsaturated monomers, cross-linking agents, catalysts, polymerization media and method for preparing the cross-linked addition copolymers in suitable particulate form are well-known in the art and reference is made thereto for the purposes of this invention. Illustrative of such patents are U.S. Pat. Nos. 2,960,480; 2,788,331; 2,642,417; 2,614,099; and 2,591,573 which teach the preparation of gel-type, cross-linked polymers and U.S. Pat. Nos. 3,637,535; 3,549,562; and 3,173,842 which teach the preparation of more porous resins, often called macroporous resins. All of the foregoing references are hereby incorporated by reference. Of the known polymerizable monoethylenically unsaturated monomers, the monovinylidene aromatic, such as styrene and monoalkyl-substituted styrenes such as vinyl toluene, ethylvinyl benzene and vinyl naphthalene, are preferred, with styrene being especially preferred. Also useful are the acrylate-containing polymers which include polymerized monomers such as methyl acrylate, butyl acrylate, methyl methacrylate, and the like. Preferred cross-linking agents include polyvinylidene aromatics such as divinyl benzene, divinyl toluene, divinyl xylene, divinyl naphthalene, trivinyl benzene, divinyl diphenyl ether, divinyl diphenyl sulfone and isopropenyl vinyl benzene; ethylene glycol dimethacrylate and divinyl sulfide, with the polyvinylidene aromatics, especially divinyl benzene, being most preferred. Also useful are the polymers formed through condensation reactions such as the phenolic and epoxyamine polymers.

The ion-exchange resin material employed herein is a synthetic polymeric ion-exchange resin containing a plurality of pendant hydroxide moieties.

One preferred class of moieties are the ammonium moieties in the hydroxide salt form. Examples of such anion-exchange resins are the resinous condensation products of aromatic amines and formaldehyde, which condensation products may be alkylated to strong base resins; condensation products of aliphatic polyamines, aldehydes or epihalohydrins and optionally, phenol; chloromethylated and aminated copolymers of monoethylenically unsaturated aromatic monomers and polyethylenically unsaturated monomers such as styrene and benzene. An example of a more preferred resin is the DOWEX ® SBR ion-exchange resins.

The pendant hydroxide-containing polymers are contacted with the 3-halo-2-hydroxyalkyl carbamates in a manner such that there is at least one equivalent of hydroxide moieties per equivalent of 3-halo-2-hydroxyalkyl carbamate. Equivalent of 3-halo-2-hydroxyalkyl carbamate means herein that amount which will react with one mole of hydroxide moieties. The equivalent ratio of hydroxides to the 3-halo-2-hydroxyalkyl carbamates is preferably between about 1:1 and 5:1, more preferably between about 1:1 and 2:1.

The reactants are contacted in a lower alkanolic solvent. Examples of lower alkanolic solvents are methanol, ethanol, propanol, butanol and pentanol. The preferred solvent is ethanol. In general, the ratio of solvent to reactants is not critical and any amount which allows the reaction to proceed is suitable. Preferably, the ratio of solvent to 3-halo-2-hydroxyalkyl carbamate is between about 10:1 and 1:1, more preferably between about 5:1 and 1:1.

This reaction step can take place at any temperature at which the reaction proceeds. Preferable temperatures are between about 0° C. and 50° C., with between about 0° C. and 20° C. being most preferred.

The process can be run at any pressure at which the reaction proceeds. Atmospheric pressure is preferred. It is preferable to run the reaction under an inert atmosphere, for example, under a nitrogen or argon atmosphere.

The 2,3-epoxyalkyl carbamates can be recovered by filtering off the ion-exchange resin. The product can then be taken up in a chlorinated hydrocarbon solvent and contacted with a mild acid, a 2-5 percent concentration of any protic acid, for example, hydrochloric acid. The organic layer can thereafter be dried over a dessicant, the solvent stripped off to leave the product which crystallizes upon standing.

Under preferred conditions, the 3-halo-2-hydroxyalkyl carbamate is prepared in 90 percent or greater yield. Under more preferable conditions, the 3-halo-2-hydroxyalkyl carbamate is prepared in 95 percent or greater yield. Under most preferred conditions, the 3-halo-2-hydroxyalkyl carbamate is prepared in 98 percent yield. Under preferred conditions, the 3-halo-2-hydroxyalkyl carbamate is prepared in 95 percent or greater purity, under most preferred conditions, 99 percent or greater purity.

Under preferred conditions, the 2,3-epoxyalkyl carbamate is prepared in 90 percent or greater yield. Under more preferable conditions, the 2,3-epoxyalkyl carbamate is prepared in 95 percent or greater yield. Under most preferred conditions, the 2,3-epoxyalkyl carbamate is prepared in 98 percent yield. Under preferred conditions, the 2,3-epoxyalkyl carbamate is prepared in 95 percent or greater purity, and under most preferred conditions, 99 percent or greater purity.

SPECIFIC EMBODIMENTS

The following examples are presented to further illustrate the invention and do not limit the scope of the invention or claims. All parts and percentages are by weight unless otherwise specified.

EXAMPLE 1

Preparation of (3-Chloro-2-hydroxy)propyl Piperidinyl Carboxylate

Distilled piperidine (4.25 g, 0.05 mole) in 25 ml of acetonitrile is added dropwise over a 30-minute period via a graduated addition funnel to a vigorously stirring solution of distilled epicarbonate of more than 99 percent purity (MW 136, 6.8 g, 0.05 mole) in 50 ml of acetonitrile. When conversion to 1,2-dichlorohydrin product is more than 98.5 percent complete, the reaction is terminated and 50 ml of diethyl ether is added, resulting in the immediate precipitation of piperidine-HCl complex. The salt complex is then removed by filtering through a medium sintered glass funnel. The filtrate is then rotary evaporated without heat leaving a crude, yellow viscous oil product. The crude oil is dissolved in anhydrous diethyl ether (100 ml), washed with a 5 percent solution of aqueous HCl, dried over magnesium sulfate and then rotary evaporated to remove the solvent. The (3-chloro-2-hydroxy)propyl piperidinyl carboxylate is obtained as a clear colorless oil (more than 99 percent purity) in approximately 80 percent yield.

EXAMPLE 2

Preparation of (3-Chloro-2-hydroxy)propyl N,N-piperazinyl Dicarboxylate

A solution of epichlorohydrin carbonate distilled to more than 99 percent purity (MW 136.5, 20.97 g, 0.15 mole) in 100 ml of acetonitrile along with sodium bicarbonate is stirred in an air atmosphere in a 250-ml round-bottom flask at about 20° C. A solution of anhydrous, sublimed piperazine (MW 86.0, 6.39 g, 0.074 mole) in 50 ml of absolute EtOH is added dropwise at a rate of 4 drops/min. The reaction is continued for 3 days at about 20° C. Isolation of the (3-chloro-2-hydroxy)propyl N,N-piperazinyl dicarboxylate is accomplished by first removing the $NaHCO_3$ by filtering through a medium sintered funnel, then removing the reaction solvent on a rotary evaporator. The concentrated reaction product containing (3-chloro-2-hydroxy)propyl N,N-piperazinyl dicarboxylate and excess epichlorohydrin is placed on a silica column (60–200 mesh) and eluted with a 50/50 solution of $CH_2Cl_2/CCl_4$. The epichlorohydrin passes through the column leaving behind the (3-chloro-2-hydroxy)propyl N,N-piperazinyl dicarboxylate product. The product is then removed from the column by elution with ethanol. After removal of ethanol via rotary evaporation, a white solid immediately forms. The solid is identified by infrared, $^1H$ nuclear magnetic resonance and elemental analysis as the (3-chloro-2-hydroxy)propyl N,N-piperazinyl dicarboxylate which has a melting point of 105° C.

EXAMPLE 3

Three grams of bis(3-chloro-2-hydroxypropyl) 1,4-piperazinyl dicarboxylate is dissolved in 50 ml of methanol. DOWEX ® SBR-10 ion-exchange resin is added. The reaction mixture is allowed to stir in a 100-ml single-necked stoppered round-bottom flask at room temperature for 41 hours. A material (2.76 g) is recovered and washed with water to remove excess or unreacted materials to give 1.29 g of the desired product, bis(2,3-epoxypropyl-) 1,4-piperazinyl dicarboxylate. The water phase is roto-evaporated to remove the water. The residue is washed with acetone to give 0.5 g of the desired product. The total yield is 1.97 g which is 82.4 percent of theoretical.

EXAMPLE 4

Distilled epichlorohydrin carbonate (20.97 g) is weighed in a 250-ml three-necked round-bottom flask equipped with magnetic stirring bar. $NaHCO_3$ (12.35 g) are added to the reaction flask followed by 100 ml of ethanol. A piperazine ethanol solution is made by utilizing very pure sublimed crystals and dissolving them in 50 ml of ethanol. The piperazine ethanol solution is then transferred to an addition funnel. While the reaction mixture is vigorously stirring at 50° C., this piperazine ethanol solution is dripped into the reaction flask at a rate of 4 drops/minute over a 5-hour period. After 72 hours, the reaction is terminated. An infrared of the product solution indicates about 10 percent of excess epihalohydrin carbonate. The $NaHCO_3$ is filtered in a medium sintered funnel. The total amount (12.35 g) was recovered. The filtrate (180 ml) is divided into two equal portions and poured into single-necked round-bottom flasks, each containing 52.0 g of DOWEX ® SBR-10 ion-exchange resin. To each flask was added 10 ml of ether bringing the total volume to 100 ml. In each flask theoretically 13.1 g of product is present. Each flask is stoppered and allowed to vigorously stir for 48 hours after which the reaction is complete. The ion-exchange resin is filtered through a coarse sintered funnel. The ethanol/ether is rotoevaporated off yielding a pale yellow to colorless oil. The viscous oil is dissolved in $CH_2Cl_2$ and washed with an aqueous solution containing about 2.5 percent hydrogen chloride and brine (50/50 50 percent hydrogen chloride and saturated sodium chloride).

The organic methylene chloride layer is then separated from the aqueous phase, dried over magnesium sulfate and filtered. The resulting bis-(2,3-epoxypropyl) piperazinyl dicarboxylate forms a white solid after removal of the $CH_2Cl_2$. The white solid is stirred in ethyl ether and filtered. The resulting bis-(2,3-epoxypropyl) piperazinyl dicarboxylate has a melting point of 85° C.–87° C.

EXAMPLE 5

Epichlorohydrin (6.8 g) is dissolved in 30 ml of acetonitrile in a 100-ml round-bottom flask. An addition funnel is placed in the single opening. To this funnel is added 5.22 ml of distilled morpholine in 10 ml of acetonitrile.

At 40° C. while the epihalohydrin carbonate is rapidly stirring, the morpholine/acetonitrile is slowly dripped in. The reaction continues from 55 to 60 hours.

The reaction is terminated when the absorption at 1800 $cm^{-1}$ is totally gone leaving an absorption band at 1700 $cm^{-1}$ for the urethane linkage. The gas chromatograph reveals most of the material is more than 96.5 percent 2-hydroxy-3-halopropyl morpholinyl carboxylate with impurities all of which are less than 0.5 percent. At about 20° C., approximately 50 ml of ether is added to the reaction. Immediately morpholine HCl precipitates out. The precipitate is filtered through a coarse sintered funnel and washed with ether. The ether/acetonitrile product is rotoevaporated to remove the two solvents. To the viscous dark yellow oil approximately 50 ml of ether is added. The ether/product solution is then washed twice with a 5 percent hydrogen chloride solution. The colored bodies go into the water phase. After rotoevaporating off the ether, a pale yellow liquid results.

To a 100-ml round-bottom flask is added 3-halo-2-hydroxypropyl morpholinyl carboxylate dissolved in 25 g of methanol. DOWEX ® SBR-10 (4 g) ion-exchange resin is added to the flask of 3-halo-2-hydroxypropyl morpholinyl carboxylate and methanol. The reaction is followed by gas chromatograph. The 3-halo-2-hydroxypropyl morpholinyl carboxylate is vigorously stirred over the resin beads at about 20° C. After 24 hours, the 3-halo-2-hydroxypropyl morpholinyl carboxylate is nearly converted to 2,3-propyl morpholinyl carboxylate. The gas chromatograph indicates a small percentage of 3-halo-2-hydroxypropyl morpholinyl carboxylate left.

What is claimed is:

1. A process for the preparation of a halohydroxyalkyl carbamate which comprises contacting an epihalohydrin carbonate with a secondary amine-containing compound, wherein the secondary amine has a pKa at which the secondary amine will react with the epihalohydrin carbonate and will not catalyze the formation of unwanted by-products, in the further presence of an acid scavenger capable of forming a salt with any hydrogen halide formed in an amount sufficient to prevent the formation of unwanted by-products from the hydrogen halides, in a polar organic solvent under conditions such that a halohydroxyalkyl carbamate, or a poly(-halohydroxyalkyl) polycarbamate is formed.

2. The process of claim 1 wherein the halohydroxyalkyl carbamate is a 3-halo-2-hydroxyalkyl carbamate.

3. The process of claim 2 wherein the secondary amine corresponds to the formula

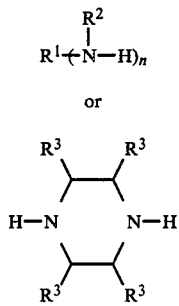

and the epihalohydrin carbonate corresponds to the formula

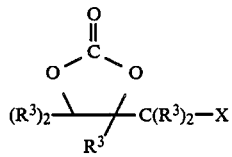

wherein
R$^1$ is separately in each occurrence an n valent aliphatic or cycloaliphatic hydrocarbon;
R$^2$ is separately in each occurrence an aliphatic or cycloaliphatic moiety;
R$^3$ is separately in each occurrence hydrogen or an aliphatic radical;
X is I, Cl or Br; and
n is an integer of 1 to 6;
wherein R$^1$ and R$^2$ may be joined to form a cycloalkylene moiety which can contain the heteroatoms O, N or S.

4. The process of claim 3 wherein the amine is an aliphatic secondary amine which corresponds to the formula

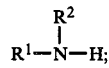

a heterocyclic secondary amine which corresponds to the formula

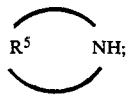

an aliphatic secondary polyamine which corresponds to the formula

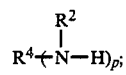

or piperazine which corresponds to the formula

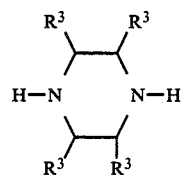

wherein
R$^1$ is separately in each occurrence an aliphatic or cycloaliphatic radical;
R$^2$ is separately in each occurrence an aliphatic or cycloaliphatic radical;
R$^3$ is separately in each occurrence hydrogen or an aliphatic radical;
R$^4$ is a p valent aliphatic or cycloaliphatic hydrocarbon;
R$^5$ is an alkylene radical which can contain a heteroatom of O, S or N which together with the nitrogen forms an aliphatic heterocyclic ring; and
p is an integer between 2 and 6, inclusive.

5. The process of claim 4 wherein the acid scavenger comprises an alkali metal bicarbonate and an alkaline earth metal bicarbonate.

6. The process of claim 5 wherein the 3-halo-2-hydroxyalkyl carbamate is a 3-halo-2-hydroxy dialiphatic or dialicyclic carbamate or a 3-halo-2-hydroxyalkyl cycloalkylene carbamate; and the poly-(3-halo-2-hydroxyalkyl) polycarbamate is a poly-(3-halo-2-hydroxyalkyl) N-aliphatic or N-alicyclic alkylene polycarbamate or a bis-(3-halo-2-hydroxyalkyl) 1,4-pyrazinyl dicarboxylate.

7. The process of claim 6 wherein the 3-halo-2-hydroxyalkyl dialiphatic or dialicyclic carbamates, 3-halo-2-hydroxyalkyl cycloalkylene carbamates and poly-(3-halo-2-hydroxyalkyl) N-dialicyclic or N-dialiphatic alkylene polycarbamates correspond to the formula

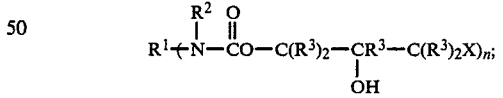

and the bis-(3-halo-2-hydroxyalkyl) 1,4-piperazinyl dicarboxylates correspond to the formula

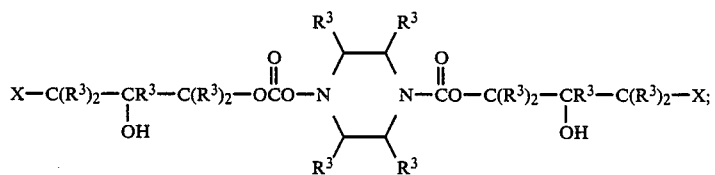

wherein $R^1$ is separately in each occurrence an n valent aliphatic or cycloaliphatic hydrocarbon;
$R^2$ is separately in each occurrence an aliphatic or cycloaliphatic moiety;
$R^3$ is separately in each occurrence hydrogen or an aliphatic moiety;
X is Br, Cl and I; and
n is an integer of 1 to 6;
wherein $R^1$ and $R^2$ may be joined to form a cycloalkylene moiety which can contain the heteroatoms O, N or S.

8. The process of claim 7 wherein the 3-halo-2-hydroxyalkyl dialiphatic or dialicyclic carbamate corresponds to the formula

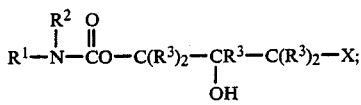

the poly-(3-halo-2-hydroxyalkyl) N-aliphatic or N-alicyclic alkylene polycarbamate corresponds to the formula

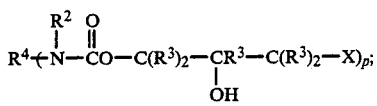

the 3-halo-2-hydroxyalkyl cycloalkylene carbamate corresponds to the formula

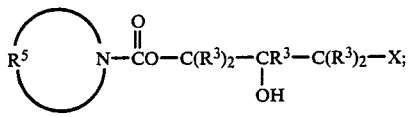

the bis-(3-halo-2-hydroxyalkyl) 1,4-piperazinyl dicarboxylate corresponds to the formula $$X-C(R^3)_2-CR^3-C(R^3)_2-OC-N \underset{R^3}{\overset{R^3}{\diamond}} N-CO-C(R^3)_2-CR^3-C(R^3)_2-X;$$
$$\phantom{XXXXX}OH\phantom{XXXXXXXXXXXXXXXXXXXX}OH$$

wherein
$R^1$ is separately in each occurrence an aliphatic or cycloaliphatic radical;
$R^2$ is separately in each occurrence an aliphatic or cycloaliphatic radical;
$R^3$ is separately in each occurrence hydrogen or an aliphatic radical;
$R^4$ is a p valent aliphatic or cycloaliphatic hydrocarbon;
$R^5$ is an alkylene radical which can contain a heteroatom of O, S or N which together with the carbamate nitrogen atom forms an aliphatic heterocyclic ring;
X is I, Cl or Br; and
p is an integer of between 2 and 6, inclusive.

9. The process of claim 8 wherein
$R^1$ is a $C_{1-20}$ aliphatic or $C_{3-20}$ cycloaliphatic radical;
$R^2$ is a $C_{1-20}$ aliphatic or $C_{3-20}$ cycloaliphatic radical;
$R^3$ is hydrogen or a $C_{1-20}$ aliphatic radical;
$R^4$ is a p valent $C_{1-20}$ aliphatic or $C_{3-20}$ cycloaliphatic hydrocarbon radical;

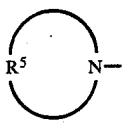

forms a piperidine, a pyrrolidine, oxazine, imidazolidine, morpholine, ethylenimine, or 3-pyrroline or perhydro-1,3-thiazine ring; and
p is the integer 2 or 3.

10. The process of claim 9 wherein
$R^1$ is $C_{1-20}$ alkyl;
$R^2$ is $C_{1-20}$ alkyl;
$R^3$ is hydrogen or $C_{1-20}$ alkyl;
$R^4$ is a p valent $C_{1-20}$ alkyl radical;

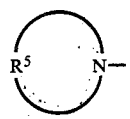

forms a piperidine, pyrrolidine, oxazine, or morpholine heterocyclic ring; and
p is 2.

11. The process of claim 10 wherein
$R^1$ is $C_{1-10}$ alkyl;
$R^2$ is $C_{1-10}$ alkyl;
$R^3$ is hydrogen or $C_{1-3}$ alkyl;
$R^4$ is $C_{1-10}$ alkyl; and

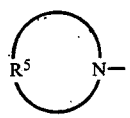

forms a pyrrolidine or piperidine ring.

12. The process of claim 11 wherein $R^3$ is hydrogen.

13. The process of claim 8 wherein the polar organic solvent is a lower alkanol, acetonitrile, tetrahydrofuran or dioxane.

14. The process of claim 13 wherein the secondary amine-containing compound is contacted with the epihalohydrin carbonate at a temperature of between about 0° C. and 100° C.

15. The process of claim 14 wherein the secondary amine-containing compound is contacted with epihalohydrin carbonate at a temperature of between about 0° C. and 40° C.

16. The process of claim 15 wherein the epihalohydrin carbonate and amine are contacted in an equivalent ratio of between 2:1 and 1:1.

17. The process of claim 16 wherein the equivalent ratio of acid scavenger to amine is between about 1:1 and 3:1.

18. The process of claim 17 wherein the equivalent ratio of acid scavenger to amine is between about 1.01:1 and 1.10:1.

19. The process of claim 18 wherein the epihalohydrin carbonate has a purity of 99 percent or greater.

20. The process of claim 3 which further comprises contacting the 3-halo-2-hydroxyalkyl dialiphatic or dialicyclic carbamate, 3-halo-2-hydroxyalkyl cycloalkylene carbamate, poly-(3-halo-2-hydroxyalkyl) N-dialicyclic or N-dialiphatic alkylene polycarbamate, or bis-(3-halo-2-hydroxyalkyl) 1,4-piperazinyl dicarboxylate, in a lower alkanol solvent with a polymer with pendant moieties which has pendant hydroxide moieties, under conditions such that the 3-halo-2-hydroxyalkyl moieties are converted to 2,3-epoxyalkyl moieties to prepare a 2,3-epoxyalkyl dialiphatic or dialicyclic carbamate, 2,3-epoxyalkyl cycloalkylene carbamate, poly-(2,3-epoxyalkyl) N-dialicyclic or N-dialiphatic alkylene polycarbamate, or a bis-(2,3-epoxyalkyl) 1,4-piperazinyl dicarboxylate.

21. The process of claim 20 wherein the 3-halo-2-hydroxyalkyl dialiphatic or dialicyclic carbamates, 3-halo-2-hydroxyalkyl cycloalkylene carbamates and poly-(3-halo-2-hydroxyalkyl) N-dialicyclic or N-dialiphatic alkylene polycarbamates correspond to the formula

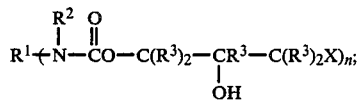

and the bis-(3-halo-2-hydroxyalkyl) 1,4-piperazinyl dicarboxylates correspond to the formula

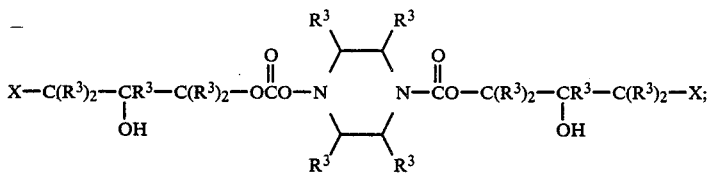

the 2,3-epoxyalkyl dialiphatic or dialicyclic carbamates, 2,3-epoxyalkyl cycloalkylene carbamates, poly-(2,3-epoxyalkyl) N-dialicyclic or N-dialiphatic alkylene polycarbamates correspond to the formula

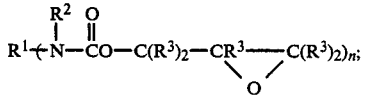

and the bis-(2,3-epoxyalkyl) 1,4-piperazinyl dicarboxylates correspond to the formula

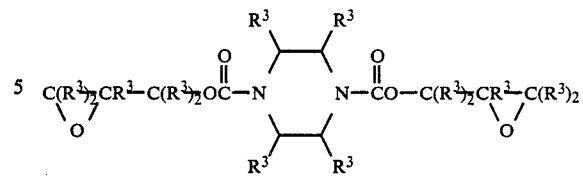

wherein $R^1$ is separately in each occurrence an n valent aliphatic or cycloaliphatic hydrocarbon;

$R^2$ is separately in each occurrence an aliphatic or cycloaliphatic moiety;

$R^3$ is separately in each occurrence hydrogen or an aliphatic moiety;

X is Br, Cl and I; and n is an integer of 1 to 6;

wherein $R^1$ and $R^2$ may be joined to form a cycloalkylene moiety which can contain the heteroatoms O, N or S.

22. The process of claim 21 wherein the 3-halo-2-hydroxyalkyl dialiphatic or dialicyclic carbamate corresponds to the formula

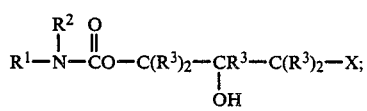

the poly(3-halo-2-hydroxyalkyl) N-aliphatic or N-alicyclic alkylene polycarbamate corresponds to the formula

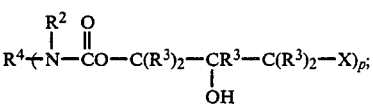

the 3-halo-2-hydroxyalkyl cycloalkylene carbamate corresponds to the formula

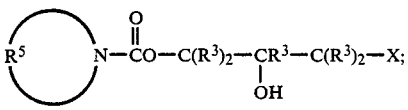

the bis-(3-halo-2-hydroxyalkyl) 1,4-piperazinyl dicarboxylate corresponds to the formula

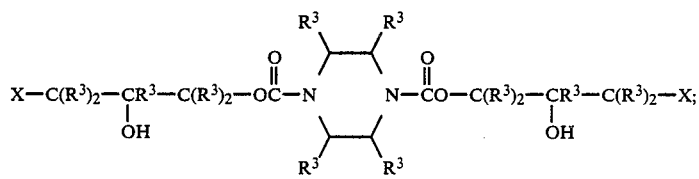

the 2,3-epoxyalkyl dialiphatic or dialicyclic carbamate corresponds to the formula $$R^1-N(R^2)-CO-C(R^3)_2-CR^3\underset{O}{\overset{}{\diagdown\diagup}}C(R^3)_2;$$

the poly(2,3-epoxyalkyl) N-aliphatic or N-alicyclic alkylene polycarbamate corresponds to the formula $$R^4(-N(R^2)-CO-C(R^3)_2-CR^3\underset{O}{\overset{}{\diagdown\diagup}}C(R^3)_2)_p;$$

the 2,3-epoxyalkyl cycloalkylene carbamate corresponds to the formula $$R^5\underset{}{\overset{}{\bigcirc}}N-CO-C(R^3)_2-CR^3\underset{O}{\overset{}{\diagdown\diagup}}C(R^3)_2;$$

and the bis-(2,3-epoxyalkyl) 1,4-piperazinyl dicarboxylate corresponds to the formula $$C(R^3)_2CR^3-C(R^3)_2OC-N\underset{R^3\ R^3}{\overset{R^3\ R^3}{\bigcirc}}N-CO-C(R^3)_2CR^3-C(R^3)_2$$

wherein
  $R^1$ is separately in each occurrence an aliphatic or cycloaliphatic radical;
  $R^2$ is separately in each occurrence an aliphatic or cycloaliphatic radical;
  $R^3$ is separately in each occurrence hydrogen or an aliphatic radical;
  $R^4$ is a p valent aliphatic or cycloaliphatic hydrocarbon;
  $R^5$ is an alkylene radical which can contain a heteroatom of O, S or N which together with the carbamate nitrogen atom forms an aliphatic heterocyclic ring;
  X is Cl, Br or I; and
  p is an integer of between 2 and 6, inclusive.

23. The process of claim 22 wherein
  $R^1$ is a $C_{1-20}$ aliphatic or $C_{3-20}$ cycloaliphatic radical;
  $R^2$ is a $C_{1-20}$ aliphatic or $C_{3-20}$ cycloaliphatic radical;
  $R^3$ is hydrogen or a $C_{1-20}$ aliphatic radical;
  $R^4$ is a p valent $C_{1-20}$ aliphatic or $C_{3-20}$ cycloaliphatic hydrocarbon radical;

$$R^5\underset{}{\overset{}{\bigcirc}}N-$$

forms a piperidine, a pyrrolidine, oxazine, imidazolidine, morpholine, ethylenimine, or 3-pyrroline or perhydro-1,3-thiazine ring; and
  p is the integer of 2 or 3.

24. The process of claim 23 wherein
  $R^1$ is $C_{1-20}$ alkyl;
  $R^2$ is $C_{1-20}$ alkyl;
  $R^3$ is hydrogen or $C_{1-20}$ alkyl;
  $R^4$ is a p valent $C_{1-20}$ alkyl radical;

$$R^5\underset{}{\overset{}{\bigcirc}}N-$$

forms a piperidine, pyrrolidine, oxazine, or morpholine heterocyclic ring; and
  p is 2.

25. The process of claim 24 wherein
  $R^1$ is $C_{1-10}$ alkyl;
  $R^2$ is $C_{1-10}$ alkyl;
  $R^3$ is hydrogen or $C_{1-3}$ alkyl;
  $R^4$ is $C_{1-10}$ alkyl; and $$R^5\underset{}{\overset{}{\bigcirc}}N-$$

forms a pyrrolidine or piperidine ring.

26. The process of claim 25 wherein $R^3$ is hydrogen.

27. The process of claim 26 wherein the epihalohydrin carbonate and amine are contacted in an equivalent ratio of between 2:1 and 1:1.

28. The process of claim 27 wherein the 3-halo-2-hydroxyalkyl carbamates are contacted with the ion-exchange resin with pendant hydroxide moieties at a temperature of between about 0° C. and 50° C.

29. The process of claim 28 wherein the solvent further comprises an organic ether.

* * * * *